United States Patent [19]

Foote

[11] Patent Number: 4,774,953
[45] Date of Patent: Oct. 4, 1988

[54] SELF-SUPPORTING TERMINAL FOR IMPLANTABLE PULSE GENERATOR AND METHOD OF MANUFACTURING THE SAME

[75] Inventor: Roger M. L. Foote, Eastwood, Australia

[73] Assignee: Telectronics, N.V., Cucacao, Netherlands Antilles

[21] Appl. No.: 33,935

[22] Filed: Apr. 3, 1987

[51] Int. Cl.[4] .................. A61N 1/00; H05G 00/00
[52] U.S. Cl. ..................... 128/419 P; 174/152 GM; 228/122; 228/263.12
[58] Field of Search ............. 128/419 P, 419 D; 174/152 GM, 50.56, 50.52, 50.61; 420/492; 228/122

[56] References Cited

U.S. PATENT DOCUMENTS

| 4,152,540 | 5/1979 | Duncan et al. | 128/419 P |
|---|---|---|---|
| 4,180,700 | 12/1979 | Kraska et al. | 174/152 |
| 4,426,033 | 1/1984 | Mizuhara | 428/606 |
| 4,445,511 | 5/1984 | Cowdery et al. | 128/419 P |
| 4,486,386 | 12/1984 | Mizuhara | 428/606 |
| 4,497,772 | 2/1985 | Mizuhara | 420/457 |
| 4,514,207 | 4/1985 | Kyle | 128/419 P |
| 4,591,535 | 5/1986 | Mizuhara | 428/627 |
| 4,604,328 | 8/1986 | Mizuhara | 428/606 |
| 4,606,978 | 8/1986 | Mizuhara | 428/606 |

Primary Examiner—William E. Kamm
Assistant Examiner—George Manuel
Attorney, Agent, or Firm—Finnegan, Henderson, Farabow, Garrett & Dunner

[57] ABSTRACT

A terminal for an implantable pulse generator for connecting an electrode lead to the generator includes a base section formed of partially stabilized zirconia (PSZ) mounted on the exterior of the pulse generator housing and a conductive terminal member coupled to the base section. The base section, terminal member and pulse generator housing are joined by a biocompatible brazing alloy which is composed, by weight, of about 13% to about 17% copper, about 13% to about 17% nickel, and the balance being titanium.

10 Claims, 1 Drawing Sheet

SELF-SUPPORTING TERMINAL FOR IMPLANTABLE PULSE GENERATOR AND METHOD OF MANUFACTURING THE SAME

BACKGROUND OF THE INVENTION

The present invention relates to a self-supporting terminal for connecting electrode leads to an implantable pulse generator, such as a cardiac pacemaker. The invention further relates to coupling a ceramic to either another ceramic or to a metal via a biocompatible active alloy.

Self-supporting terminals for implantable pulse generators, such as cardiac pacemakers, are generally disclosed in U.S. Pat. No. 4,445,511, which discloses a terminal comprising an alumina ceramic base brazed to a metal terminal piece such as titanium. The ceramic base has a generally cylindrical shape which surrounds the base of the terminal piece. A hole is provided in the upper section of the terminal piece to facilitate the insertion of an electrode lead, which can be fixed in place by means of a screw (such as a grub screw) which is located in the upper section of the terminal piece and disposed so as to project into the path of the lead once it is located in the hole.

The afore-described terminal is subjected to torque from several sources, however. During tightening of the screw to hold the electrode lead in place, for example, a wrench is commonly used which exerts major torque on the terminal. Also, insertion or withdrawal of the electrode lead can result in the application of a sideways, i.e., horizonaal force to the terminal. Any of these forces may be sufficient to destroy the coupling between the ceramic base and terminal piece or pacemaker, thereby destroying the integrity of the terminal.

An important consideration in implantable pulse generators is compactness of the device. As connection terminals are made smaller, alumina ceramics known in the current art of self-supporting terminals lack the necessary strength to withstand the sideways and flexural torque exerted during implantation and adjustment of the pacemaker. To ensure that sufficient strength is provided, severe limitations on the dimensions of the terminal are therefore present. A need is apparent in the art for terminals of sufficient strength yet which have dimensions smaller than the alumina ceramic terminals now in use.

For example, the sideways bending strength S of a connector terminal has been found to be proportional to the cube of the diameter D of a terminal having a cylindrical configuration, i.e., $S = D^3$. The following table shows the relationship between terminal diameter reduction and required increase in material strength in order to withstand the same sideways load:

| Terminal Diameter | Increase in Material Strength Required | Strength Using Current Material |
| --- | --- | --- |
| 1.0 D | 0% | 1.0 S |
| 0.9 D | 37% | 0.73 S |
| 0.8 D | 95% | 0.51 S |
| 0.7 D | 192% | 0.34 S |
| 0.6 D | 363% | 0.22 S |
| 0.5 D | 700% | 0.13 S |

Accordingly, presently-used ceramics cannot achieve a sufficient reduction in size or dimension of the connector terminal without the accompanying loss of sideways or flexural strength, as shown above. Specifically, known terminals utilizing alumina ceramics do not have sufficiently high sideways bending or flexural strengths, so suitable reductions in terminal dimensions cannot be achieved.

A further problem associated with the alumina ceramic used in current devices is the possibility of cracking the ceramic during the brazing cycle. In the brazing process, such as shown in U.S. Pat. Nos. 4,426,033 and 4,591,535, the terminal is heated to a brazing temperature followed by a cooling down period. If this cooling down phase is too fast, the alumina ceramic has a tendency to crack due to its low thermal shock resistance. A superior ceramic and brazing alloy is therefore needed in the art of self-supporting terminals.

SUMMARY OF THE INVENTION

It is therefore an object of the present invention to provide a self-supporting terminal having increased flexural strength for connecting an electrode lead to an implantable pulse generator.

A further object of the invention is to provide a self-supporting terminal of reduced dimensions for an implantable pulse generator characterized by reduced diameter and height over prior art devices, thereby allowing for a more compact implantable generator.

Another object of the invention is to provide a self-supporting terminal comprising a ceramic having a high thermal shock resistance whereby cracking during a cool down phase is avoided. Accordingly, a faster brazing cycle can be employed, resulting in improved cost-efficiency and faster processing time in the manufacture of such terminals.

Additional objects and advantages of the invention will be set forth in part in the description which follows, and in part will be obvious from the description or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the invention includes a terminal for an implantable pulse generator for connecting an electrode lead to the generator, the terminal comprising: an exterior base section formed of partially stabilized zirconia, the base section being mounted on the generator; and a metallic terminal member including means for receiving the electrode lead, the member being supported by the base section. In particular, the base section, terminal member and pulse generator are coupled by means of a biocompatible active alloy braze.

The accompanying drawing, which is incorporated in and constitutes part of this specification, illustrates one embodiment of the invention and, together with the following description, serves to explain the principles of the invention.

DESCRIPTION OF THE PREFERRED EMBODIMENT

Figure 1:
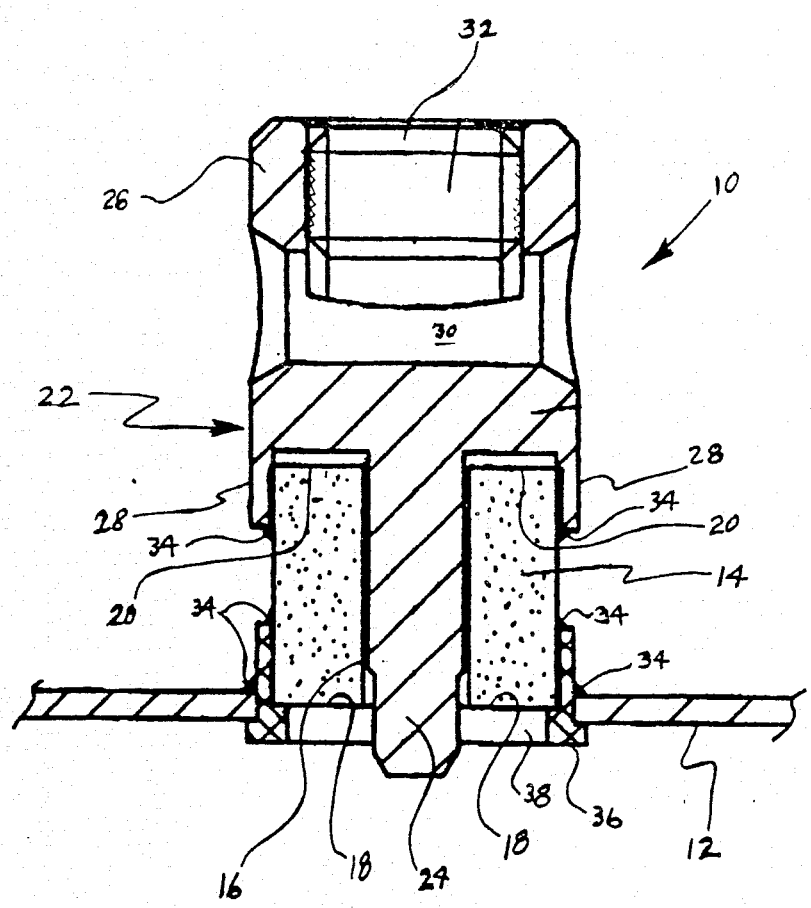
FIG. 1 is a cross section of a self-supporting terminal and pulse generator in accordance with the present invention.

Reference will now be made in detail to the presently preferred embodiment of the invention, an example of which is illustrated in the accompanying drawings. Throughout the drawings, like reference characters are used to designate like elements.

Figure 2:
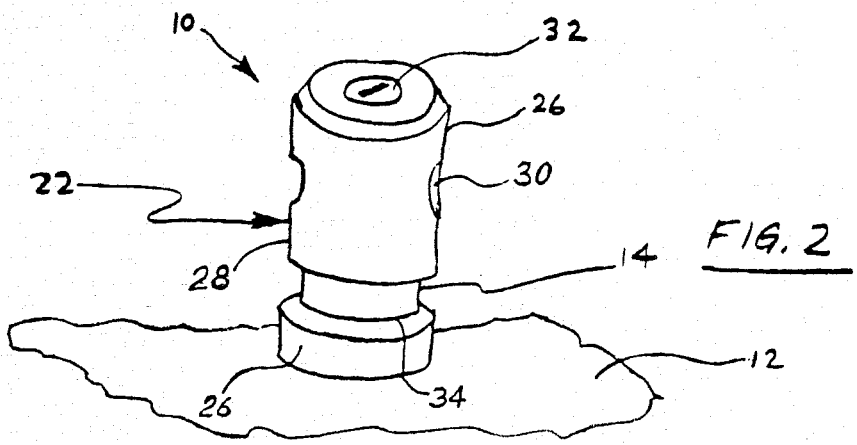
FIG. 2 is a top perspective view of the terminal of FIG. 1.

FIG. 1 illustrates a cross section of a preferred embodiment of a self-supporting terminal 10 for an implantable pulse generator, such as a cardiac pacemaker (not shown in full). Terminal 10 is also shown in perspective view in FIG. 2. The terminal 10 is mounted externally on a wall 12 of the housing of the pulse generator. The terminal 10 may serve, for example, to connect an electrode lead (not shown) to electronics housed within the wall 12 of the pulse generator.

In accordance with the present invention, the terminal comprises an exterior base section formed of partially stabilized zirconia, the base section being mounted on the pulse generator. As embodied herein, the base section comprises base 14 which is preferrably formed of partially stablized zirconia ("PSZ") ceramic using magnesium oxide or yttrium oxide as a stabilizer. The PSZ substrate can be processed to remove any irregularities from its surface, such processing being most easily achieved by grinding as the toughening behavior of PSZ permits formation of a defect-free surface. As shown in cross section in FIG. 1, PSZ substrate 14 is preferably formed as a cylinder having a central aperture 16 and first and second end faces 18 and 20, respectively.

Also in accordance with the present invention, a metallic terminal member is provided, including means for receiving the electrode lead, the terminal member being supported by the base section. As embodied herein, the terminal member is generally designated by reference character 22 in the drawing. In a preferred embodiment, terminal member 22 includes a shaft portion 24 and an electrode lead receiving portion 26. These two portions may be integrally formed of a conducting material, such as aluminum, titanium or other metals suitable for implantation in the body.

As shown in FIG. 1, shaft portion 24 is disposed within central aperture 16 of base member 14 so that second face 20 of the base member substantially abuts the corresponding face of electrode receiving portion 26. Terminal member 22 is thus seated on and supported by base member 14. To ensure sound placement of these two elements, terminal member 22 may include a flange 28 having an interior diameter substantially identical to the exterior diameter of base member 14, as shown in FIG. 1.

The electrode lead receiving portion 26 of terminal member 22 includes a hole 30 having a diameter sufficient to receive the tip of an electrode lead (not shown). To secure the lead in place within hole 30, a grub screw 32 may be provided which has a threaded portion and an end protruding into hole 30. Once the lead is in place in hole 30, grub screw 32 is tightened so as to firmly entrap the electrode lead and thereby ensure consistent electrical and mechanical interconnection.

According to the present invention, the terminal member, base member and pulse generator are coupled together by a biocompatible alloy braze. As shown in the drawings, this braze is indicated by reference character 34 and is applied at the junction of base member 14 and flange 28 of terminal member 22. Braze 34 may also be applied at the junction of base member 14 and pulse generator housing 12 through the intermediary of a collar 36 having a generally circular shape suitable to encapture first face 18 of base member 14. A disk 38 may also be provided abutting first face 18 and contacting, along its outer periphery, collar 36.

Electrical interconnection between the electrode lead and circuitry (not shown) within the pacemaker can be accomplished by soldering or otherwise coupling a wire or other conductor to the end of shaft 24 that is disposed in the interior of pacemaker housing 12. In such a case, i.e., where no connection between terminal member 22 and housing 12 is desired, either one or both collar 36 and disk 38 are non-conductive and can be formed of ceramic or other insulating material. Alternately, these elements can be eliminated altogether so that base member 14 is brazed directly to housing 12 during construction of the overall device.

Where it is desired to electrically interconnect the electrode lead and housing 12, collar 36 and disk 38 can be made of metal or another conductive material.

The particular interconnection between the terminal member and pulse generator (housing or internal circuitry) is considered obvious to practitioners of ordinary skill in light of this disclosure, and variations in such interconnection—including elimination and/or substitution of various elements for collar 36 and disk 38—can be made without departing from the spirit or scope of the present invention. The invention is more directly concerned with the employment of a PSZ base member and a biocompatible alloy braze for construction of the overall device, as it is these features which particularly contribute to the reductions in size of the inventive terminal while allowing the necessary strength and torque resistance to be maintained.

In accordance with the preferred embodiment, braze 34 is biocompatible and corrosion-resistant. The approximate composition of braze 34 is, by weight, from about 13% to about 17% copper, from about 13% to about 17% nickel, with the balance being titanium. A suitable alloy braze meeting these requirements is available from the WESGO Division of GTE Products Corporation of Belmont, California and is sold under the tradename "Ticuni".

To construct the terminal according to the present invention, the PSZ base element is first processed, such as by grinding, to remove irregularities and form a defect-free surface. The base element is then assembled in a close fitting fashion to the terminal member and collar/disk (if any) and the active brazing alloy is placed in a position as to enable the braze to flow between the PSZ and member interface when the overall assembly is heated to the flow temperature of the brazing alloy. This may be done, for example, by placing a foil of brazing alloy between the PSZ element and adjacent member; alternately, braze alloy in the form of powder can be adhered to the interface joining surfaces by a clear lacquer whereafter the braze can flow into the joint interface when the assembly is heated to the flow temperature of the braze alloy.

A fast brazing cycle can be used due to the much higher thermal shock resistance exhibited by the PSZ ceramic in comparison with alumina ceramics. This particular advantage eliminates destruction of the terminal due to problems such as cracking during the brazing cycle. This leads to reductions in processing time and increases in cost effectiveness.

As can be appreciated from the structure described above and shown in FIGS. 1 and 2, a terminal constructed according to the present invention may present joints formed of either PSZ ceramic with metal or PSZ ceramic with other ceramics and insulating materials. Ideally, the member to be brazed to the PSZ ceramic has thermal expansion properties similar to that of the PSZ material. By way of example and without intending to limit the present invention, the following materials can be brazed to PSZ ceramic through use of the "Ticuni" brazing alloy and application of a flow temperature of 1100° C.: PSZ ceramic, titanium, stainless steel and aluminium oxide. Thus, a wide range of materials can be employed for the terminal member, collar, disk and pulse generator housing without departing from the spirit and scope of the present invention.

The PSZ ceramic used in the aforedescribed embodiment of the invention has a sideways bending strength or flexural strength that is approximate 80% greater than that of alumina ceramic. Since compactness is a critical factor in the design of implantable pulse generators, such as pacemakers, the present invention allows for a terminal of reduced dimension without loss of bending strength or flexural strength.

Other embodiments of the invention will be apparent to those skilled in the art from consideration of the specification and practice of the invention disclosed herein. Thus, it is intended that the specification and drawing be considered as exemplary only, with the true scope and spirit of the invention being indicated by the following claims.

What I claim is:

1. A terminal for an implantable pulse generator for connecting an electrode lead to the generator, the terminal comprising:
   an exterior base section formed of partially stabilized zirconia, said base section being mounted on the generator; and
   a metallic terminal member including means for receiving the electrode lead, said member being supported by said base section.

2. A terminal as recited in claim 1, wherein said base section is coupled to the generator and to the terminal member by a brazing alloy.

3. A terminal as recited in claim 2, wherein said brazing alloy comprises a biocompatible active material.

4. A terminal as recited in claim 2, wherein said brazing alloy consists essentially by weight of about 13% to about 17% copper, about 13% to about 17% nickel, and any balance being titanium.

5. A terminal as recited in claim 1, wherein said receiving means comprises a hole in said terminal member for receiving the electrode lead, and a screw disposed in said terminal member and projecting into the hole for maintaining the electrode lead in place within the hole.

6. A terminal as recited in claim 1, wherein said terminal member includes a shaft portion extending from said receiving means, and said base section is disposed about said shaft portion so as to separate said receiving means from the pulse generator.

7. A terminal for an implantable pulse generator for connecting an electrode lead to the generator, the terminal comprising:
   a base section formed of partially stabilized zirconia coupled to an exterior portion of the pulse generator; and
   a metallic terminal member having a shaft portion coupled to a lead receiving portion, said shaft portion being encircled by said base section for supporting said terminal member and separating said lead receiving portion from the exterior portion of the pulse generator.

8. A terminal as recited in claim 7, wherein said base section comprises partially stabilized zirconia using a stabilizer selected from a group consisting of magnesium oxide and yttrium oxide.

9. A terminal as recited in claim 7, wherein said base section is coupled to said terminal member via a brazed alloy.

10. A method of manufacturing a terminal for an implantable pulse generator for connecting an electrode lead to the generator, the method comprising:
    providing an exterior base section formed of partially stabilized zirconia, said base section being adapted for mounting on the generator; and
    brazing to said base section a metallic terminal member including means for receiving the electrode lead, said metallic member being supported by said base section, said brazing step involving a biocompatible alloy consisting essentially by weight of about 13% to about 17% copper, about 13% to about 17% nickel, and any balance being titanium.

* * * * *